US009944718B2

(12) United States Patent
Young et al.

(10) Patent No.: US 9,944,718 B2
(45) Date of Patent: Apr. 17, 2018

(54) ADAM22 FOR USE AS A PROGNOSTIC VARIABLE, AND TARGET FOR THERAPY, OF A METASTATIC BREAST CANCER DISEASE

(71) Applicant: Royal College of Surgeons in Ireland, Dublin (IE)

(72) Inventors: Leonie Young, Dublin (IE); Damian McCartan, Dublin (IE); Christopher Byrne, Dublin (IE)

(73) Assignee: ROYAL COLLEGE OF SURGEONS IN IRELAND, Dublin (IE)

(*) Notice: Subject to any disclaimer, the term of this patent is extended or adjusted under 35 U.S.C. 154(b) by 0 days.

(21) Appl. No.: 15/005,523

(22) Filed: Jan. 25, 2016

(65) Prior Publication Data
US 2016/0137748 A1 May 19, 2016

Related U.S. Application Data

(63) Continuation of application No. 14/356,012, filed as application No. PCT/EP2012/071864 on Nov. 5, 2012, now Pat. No. 9,285,370.

(30) Foreign Application Priority Data

Nov. 4, 2011 (EP) .................................. 11187962

(51) Int. Cl.
| | |
|---|---|
| A61K 39/00 | (2006.01) |
| C07K 16/40 | (2006.01) |
| G01N 33/574 | (2006.01) |
| A61K 38/17 | (2006.01) |
| C07K 16/30 | (2006.01) |

(52) U.S. Cl.
CPC .......... *C07K 16/40* (2013.01); *A61K 38/1709* (2013.01); *C07K 16/3015* (2013.01); *G01N 33/57415* (2013.01); *C07K 2317/76* (2013.01); *G01N 2333/96419* (2013.01); *G01N 2800/52* (2013.01)

(58) Field of Classification Search
None
See application file for complete search history.

(56) References Cited

U.S. PATENT DOCUMENTS

| 6,057,105 A | 5/2000 | Hoon et al. |
| 2005/0001006 A1 | 1/2005 | Ueno |
| 2005/0221376 A1 | 10/2005 | Young et al. |

FOREIGN PATENT DOCUMENTS

| WO | WO2000043493 | * 7/2000 |
| WO | 2013064699 A1 | 5/2013 |

OTHER PUBLICATIONS

McCartan and Leonie Young et al, Cancer Res, 72:220-9, Epub: Nov. 9, 2011.*
Database ArrayExpress (Online), "Experiment E-GEOD-28987", Nov. 2011, retrieved from EBI, database accession No. E-GEOD-28987 abstract.*
Dillon, Mary F et al., "Cyclooxygenase-2 Predicts Adverse Effects of Tamoxifen: A Possible Mechanism of Role for Nuclear HER2 in Breast Cancer Patients", Endocrine-Relat Cancer, 2008, vol. 15, pp. 745-753.*
Fukata, Yuko et al., "Epilepsy-Related Ligand/Receptor Complex LGI1 and ADAM22 Regulate Synaptic Transmission", American Association for the Advancement of Science, Sep. 2006, vol. 313, No. 5794 pp. 1792-1795.*
Gabellini, Nadia et al., "Increased Expression of LGI1 Gene Triggers Growth Inhibition and Apoptosis of Neuroblastoma Cells", Journal of Cellular Physiology, Jun. 2006, vol. 207, No. 3, pp. 711-721.*
Gabellini, N. et al., "Expression of LGI1 Impairs Proliferation and Survival of HeLa Cells", International Journal of Cell Biology, 2009, vol. 2009, Article ID 417197, 6 pages*.
Harvey, Jennet M et al., "Estrogen Receptor Status by Immunohistochemistry is Superior to the Ligand-Binding Assay for Predicting Response to Adjuvant Endocrine Therapy in Breast Cancer", Journal Clinical Oncology, May 1999, vol. 17(5), pp. 1474-1481.*
Kunapuli, Padmaja et al., "LGI1, a Putative Tumor Metastasis Suppressor Gene, Controls in Vitro Invasiveness and Expression of Matrix Metalloproteinases in Glioma Cells through the ERK1/2 Pathway", Journal of Biological Chemistry, Feb. 2004, vol. 279, No. 22, pp. 23151-23157.*
McCartan, Damian et al., "Global Characterization of the SRC-1 Transcriptome Identifies ADAM22 as an ER-Independent Mediator of Endocrine-Resistant Breast Cancer", Cancer Research, Nov. 2011, vol. 72, No. 1, pp. 220-229.*
Sagane, Koji et al., "LGI1 and LGI4 Bind to ADAM22, ADAM23 and ADAM11", International Journal of Biological Science, 2008, vol. 4(6), pp. 387-396.*
International Search Report for Application No. PCT/EP12/071864 dated Jan. 21, 2013, 5 pages*.
International Preliminary Report on Patentability for Application No. PCT/EP12/071864 dated May 6, 2014, 12 pages*.
Wolfsberg, T.G. et al., "ADAM, a Novel Family of Membrane Proteins Containing a Disintegrin and Metalloprotease Domain: Multipotential Functions in Cell-Cell and Cell-Matrix Interactions", The Journal of Cell Biology, Oct. 1995, vol. 131, pp. 275-278.*
Office Action received in U.S. Appl. No. 14/356,012, filed Apr. 27, 2015, 85 pages.*

(Continued)

*Primary Examiner* — Lei Yao
(74) *Attorney, Agent, or Firm* — Pierce Atwood LLP

(57) ABSTRACT

A method of diagnosing metastatic potential of a breast cancer in an individual with breast cancer is described. The method comprises a step of assaying a breast cancer tumor sample from the patient for expression of A Disintegrin And Metalloproteinase 22, (ADAM22), wherein expression of ADAM22 correlates with increased potential for metastasis compared with a patient who is ADAM22 negative. The invention also describes an agent for use in the treatment of metastatic breast cancer in a patient, in which the agent is selected from leucine-rich, glioma-inactivated protein 1 (LGI1) protein (SEQ ID NO:1) and an LGI1 peptide mimic capable of mimicking the ADAM22 binding activity of LGI1 by binding to the LGI1 binding domain of ADAM22 (SEQ ID NO: 4) and which is capable of inhibiting migration of endocrine resistant breast cancer cells.

4 Claims, 2 Drawing Sheets

(56) References Cited

OTHER PUBLICATIONS

Response to Office Action dated Apr. 27, 2015 received for U.S. Appl. No. 14/356,012, filed Sep. 28, 2015, 19 pages.*
Supplemental response U.S. Appl. No. 14/356,012, filed Oct. 20, 2015, 4 pages.*
Breast Cancer-Merck Manual, from http://www.merckmanuals.com/professional/gynecology_and_obstetrics/breas_disorders/br . . . , pp. 1-12, accessed Apr. 9, 2015.*
Bolger et al, ADAM22 as a Prognostic and Therapeutic Drug Target in the Treatment of Endocrine-Resistant Breast Cancer, Vitamins and Hormones, 2013, 93, pp. 307-321.*
Chikina et al, the Cellular Mechanisms and Regulation of Metastasis Formation, Molecular Biology, 2014, 48, pp. 165-180.*
D'Abaco et al, ADAM22, Expressed in Normal Brain But Not in High-Grade Gliomas, Inhibits Cellular Proliferation Via the Disintegrin Domain, Neurosurgery, 2006, 58, pp. 179-186.*
Lorusso et al, New insights into the mechanisms of organ-specific breast cancer metastasis, Seminars in Cancer Biology, 2012, 22, pp. 226-233.*
Zheng et al, ADAM17 promotes breast cancer cell malignant phenotype through EGFR-PI3K-AKT activation, Cancer Biology & Therapy, 2009, 8, pp. 1045-1054.*
U.S. Appl. No. 14/356,012, filed May 2, 2014, Allowed.

* cited by examiner

ADAM22 FOR USE AS A PROGNOSTIC VARIABLE, AND TARGET FOR THERAPY, OF A METASTATIC BREAST CANCER DISEASE

RELATED APPLICATIONS

This application is a continuation of U.S. Ser. No. 14/356,012 filed May 2, 2014, now pending, which is a National Stage Filing under U.S.C. § 371 of PCT International Application PCT/EP2012/071864, filed Nov. 5, 2012, which designates the U.S., and which claims benefit European Application No. 11187962.3 filed Nov. 4, 2011, the entire contents of each of which is incorporated herein by reference.

SEQUENCE LISTING

The instant application incorporates by reference the Sequence Listing in the ASCII text file filed May 2, 2014, entitled "P10757PC00_ST25.txt", which file was created on Apr. 17, 2014, the size of which file is 16440 bytes.

TECHNICAL FIELD

The invention relates to a method of assessing the metastatic status of a breast cancer in a breast cancer patient. Furthermore the invention relates to the treatment or prevention of metastatic breast cancer. The invention also encompasses a companion diagnostic for the directed use of the therapy to treat metastatic breast cancer.

BACKGROUND TO THE INVENTION

Current Endocrine Treatment in Breast Cancer

Breast cancer continues to affect one woman in ten in the western world, and despite significant treatment advances in recent years, the mortality rate still remains at around 35%. Current endocrine therapies are based on manipulating the estrogen receptor (ER) either directly with ER modulators such as tamoxifen, or by reducing levels of circulating estrogen with aromatase inhibitors (AIs). The development of third-generation aromatase inhibitors (AIs) has changed therapy in post-menopausal patients with hormone-sensitive breast cancer. There are two main types of AIs: irreversible steroidal inhibitors exemplified by exemestane, and non-steroidal inhibitors such as anastrozole and letrozole which are competitive reversible inhibitors. Randomized clinical trials, including several led by our group, have demonstrated prolongation of disease-free survival in patients with early stage breast cancer.

Regardless of the age of the patient, adjuvant endocrine therapy offers substantial benefit in terms of reduction in risk of tumour recurrence in women with ER-positive tumours. However, while most patients initially respond to tamoxifen, in 30-40% of cases these tumours have metastatic disease within 5 years. This common clinical scenario precipitates cessation of the regime and the initiation of second line therapy. Uncovering the key mechanisms involved in the development of metastasis provide predictive markers of disease recurrence which will enable the tailoring of existing therapies and the development of new drugs in this class, to improve outcome in specific patient groups.

Biomarkers of Endocrine Sensitivity in Breast Cancer Patients

Classic pathologic parameters, such as tumour size, grade, ER and HER2 status have been invaluable in informing the clinical management of breast cancer; however, a significant number of patients with a good prognostic profile will have a tumour recurrence. More recently, with the advent of gene expression profiling research, additional mechanisms to predict disease recurrence are now available. Technologies provided by Agendia (MammaPrint) and Genomic Health (OncotypeDx) which involve detection of a panel of genes performed by the providing companies have reported independent hazard ratios of 2.23 and 3.21 respectively. The predictive value of these tests is greater than any of the currently employed pathological parameters including ER and HER2 (hazard ratios 0.665 and 1.505, respectively). Elucidation of the mechanisms of how a tumour can adapt to endocrine therapy and consequently reoccur will provide mechanistically anchored predictive biomarkers, which can easily be detected and used in the clinic to select appropriate treatments.

New Therapeutics for the Treatment of Metastatic Disease

There are no targeted therapies currently available that act to specifically inhibit metastasis in breast cancer. Most patients are treated with chemotherapy or radiotherapy which does not specifically target cancer cells. Classic DNA-damaging cytotoxic drugs (eg. cyclophosphamide, doxorubicin, 5-fluorouracil) are still the mainstay of treatment regimens, and, although crude, are effective. Current directed therapies against metastatic cancers only inhibit angiogenesis. In doing so, they cut off nutrient supply and inhibit access of metastatic cells to the blood stream. The anti-angiogenic, AVASTIN® (bevacizumab) (Roche) is used to treat a range of cancers, including colorectal, lung, and kidney cancer. Its use in metastatic breast cancer however is controversial. The FDA recently withdrew approval for its use in the metastatic setting and the European Commission has only approved it in combination with the chemotherapy drugs Paclitaxel or XELODA® (capecitabine). There is therefore a pressing need in terms of healthcare and economics to develop new directed therapies to treat metastatic breast cancer.

It is an object of the invention to overcome at least one of the above-referenced problems.

STATEMENTS OF INVENTION

The Applicant has identified a marker of breast tumour metastasis, ADAM22 (SEQ ID NO: 2), that can be detected in patient tumour tissue and which functions as a prognostic variable of breast cancer metastatic disease (i.e. the presence of the marker independently correlates with an increased risk of metastasis, and reduced disease free survival, compared with an individual who is negative for the marker). The Applicant has also discovered that ADAM22 is involved in the development and pathology of a metastatic phenotype and that the protein can therefore be targeted in treatment of a metastatic phenotype of breast cancer.

Thus, in a first aspect, the invention relates to a method or assay of diagnosing metastatic potential of a breast cancer in an individual with breast cancer, the method comprising a step of assaying a sample (i.e. of breast tumour tissue) from the patient for expression of ADAM22, wherein expression of ADAM22 correlates with increased metastatic potential (or reduced disease free survival) compared with a patient who is ADAM22 negative.

In a second aspect, the invention relates to a method of treatment or prevention of metastatic breast cancer in a patient, the method comprising a step of administering to the individual a therapeutically effective amount of an ADAM22 inhibitor. Preferably, the ADAM22 inhibitor is selected from an oligonucleotide capable of attenuating the function of ADAM22, LGI1 protein (SEQ ID NO: 1) or a functional variant thereof, or a LGI1 peptide mimic.

In a third aspect, the invention relates to a method of treatment or prevention of metastatic breast cancer in a breast cancer patient, the method comprising a step of administering to the individual a therapeutically effective amount of an ADAM22 inhibitor, wherein the breast cancer patient is ADAM22 positive. Preferably, the ADAM22 inhibitor is selected from an oligonucleotide capable of attenuating the function or expression of ADAM22, LGI1 protein (SEQ ID NO: 1) or a functional variant thereof, or a LGI1 peptide mimic.

The invention also relates to a kit for detection of ADAM22 as a companion diagnostic in the treatment/prevention of metastatic breast cancer by inhibition of ADAM22. Thus, in a fourth aspect, the invention relates to a kit comprising means for detecting whether a patient is ADAM22 positive or ADAM22 negative and a pharmaceutical composition comprising a therapeutically effective amount of an ADAM22 inhibitor. Preferably, the ADAM22 inhibitor is selected from an oligonucleotide capable of attenuating the function or expression of ADAM22, LGI1 protein (SEQ ID NO: 1) or a functional variant thereof, or a LGI1 peptide mimic.

The invention relates to a method of or assay for of identifying a breast cancer patient suitable for treatment of metastatic breast cancer with an ADAM22 inhibitor, the method comprising a step of assaying a sample (i.e. of breast tumour tissue) from the patient for expression of ADAM22, wherein expression of ADAM22 indicates that the patient is suitable for treatment with an ADAM22 inhibitor.

The invention also relates to an ADAM22 inhibitor for use as a medicament. Preferably, the ADAM22 inhibitor is selected from an oligonucleotide capable of attenuating the function or expression of ADAM22, LGI1 protein (SEQ ID NO: 1) or a functional variant thereof, or a LGI1 peptide mimic.

The invention also relates to a pharmaceutical composition comprising an ADAM22 inhibitor and a pharmaceutically acceptable carrier. Preferably, the ADAM22 inhibitor is selected from an oligonucleotide capable of attenuating the function or expression of ADAM22, LGI1 protein (SEQ ID NO: 1) or a functional variant thereof, or a LGI1 peptide mimic.

In the assays of the invention, the step of assaying a sample of breast tumour tissue from the patient for expression of ADAM22 is preferably at least partly performed with a non-human machine, for example a computer.

The invention also provides a computer program comprising program instructions for causing a computer to perform the method of the invention.

The invention also relates to a system for obtaining data from at least one test sample obtained from at least one individual, the system comprising:
  a determination module configured to receive at least one test sample and perform at least one test analysis on the test sample to assay for the expression of ADAM22;
  optionally, a storage system for ADAM22 expression data generated by the determination system; and
  a display module for displaying a content based in part on the data output from said determination module, wherein the content comprises a signal indicative of the expression of ADAM22.

The invention also relates to a system according to the invention for diagnosing metastatic potential of a breast cancer in an individual with breast cancer, in which the system comprises a correlation module for correlating ADAM22 expression data from the determination module with metastatic potential of breast cancer, wherein the expression of ADAM22 correlates with increased potential for metastasis compared with a patient who is ADAM22 negative, and wherein the display module displays a content based in part on the data from the correlation system, the content optionally comprising a signal indicative of the metastatic potential of the breast cancer.

The invention also relates to a system according to the invention for identifying a breast cancer patient suitable for treatment of metastatic breast cancer with an ADAM22 inhibitor, in which the system comprises a correlation module for correlating ADAM22 expression data from the determination module with suitability for treatment of metastatic breast cancer with an ADAM22 inhibitor, wherein the expression of ADAM22 indicates that the patient is suitable for treatment with an ADAM22 inhibitor, and wherein the display module displays a content based in part on the data from the correlation system, the content optionally comprising a signal indicative of the suitability for treatment of metastatic breast cancer with an ADAM22 inhibitor.

Typically, the determination system comprises an immunohistochemical detection apparatus.

The invention also relates to an assay for identifying an agent capable of treating or preventing metastasis of a breast cancer, the method comprising the step of providing a sample of endocrine-resistant breast cancer cells, incubating the sample with a test agent, and detecting binding between the test agent and an LGI1 binding site of ADAM22 expressed by the cells, wherein a test agent that binds to the LGI1 binding site of ADAM22 is an agent capable of treating or preventing metastasis of a breast cancer.

(G) Daily inject of LGI1 inhibits cell proliferation and metastasis of endocrine resistant LetR cells in vivo.

DETAILED DESCRIPTION OF THE INVENTION

Figure 1:
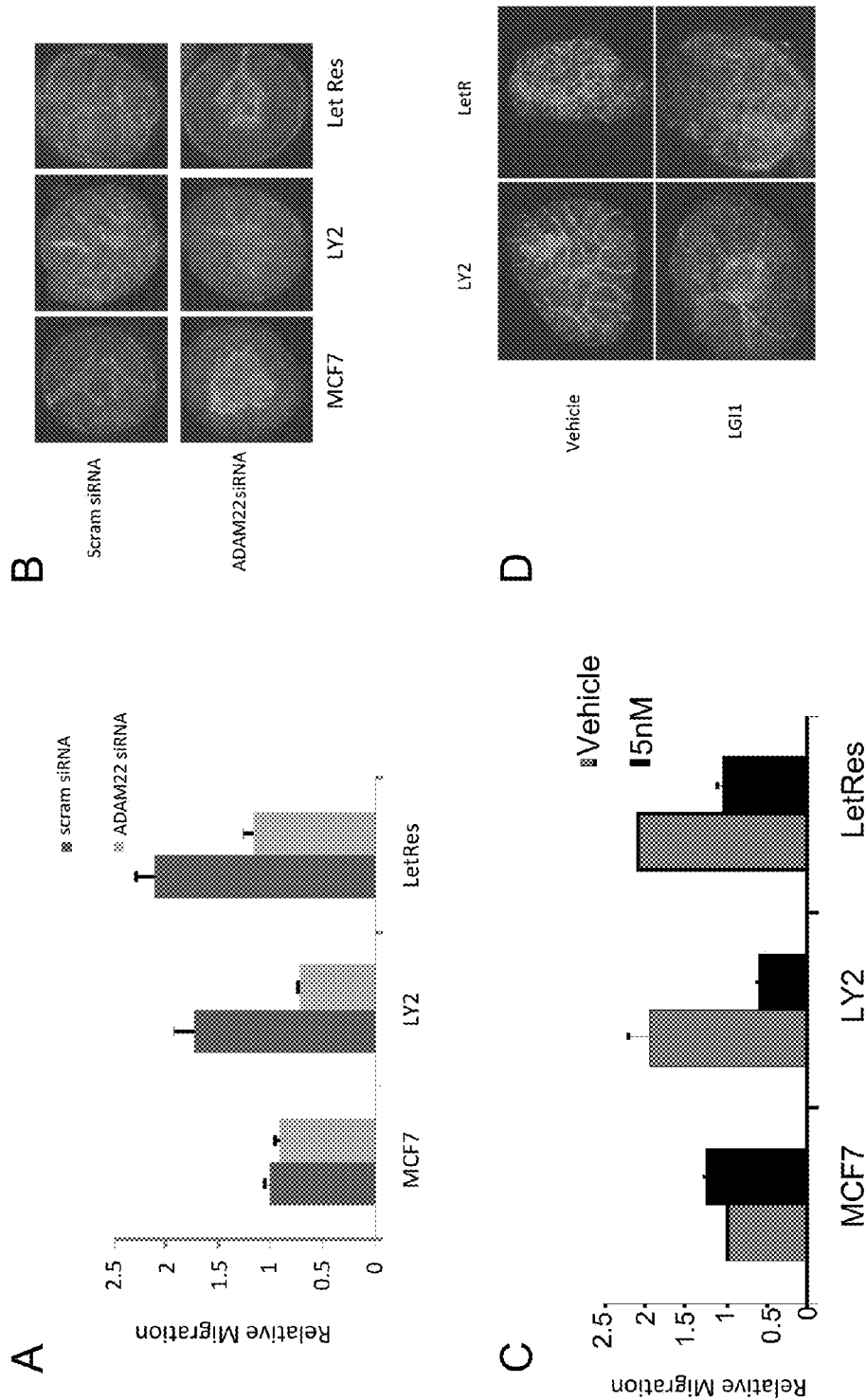
FIG. 1: ADAM22 promotes tumour progression in endocrine resistant breast cancer.
(A) A histogram representing the migration pattern of MCF7, LY2 and letrozole resistant (LetR) cells following transient transfection with scrambled (scr) siRNA or ADAM22 siRNA. Average migration is given as a ratio to scr-siRNA in MCF-7 cells. Results are expressed as mean±SD, n=3.
(B) Endocrine resistant cells (LY2 and LetR) have reduced cellular differentiation as exemplified by their inability to form acni in 3D culture in comparison to endocrine sensitive MCF-7 cells, this was restored by knockdown of ADAM22 with siRNA (n=3).
(C) Treatment of endocrine resistant LY2 and LetR cells with recombinant LGI1 (5 nM) significantly reduced cellular migration. There was no discernable effect of LGI1 on migration of MCF7 cells. Average migration is given as a ratio to MCF-7 cells. Results are expressed as mean ±SD, n=3.
(D) Treatment of LetR cells with LGI1 restored cellular differentiation (n=3).
(E) The LGI1 mimetic (SEQ ID NO: 5) (5 nM) inhibits cell migration of endocrine resistant LY2 and LetR cells.
(F) Toxicity study of LGI1 peptide mimetic in vivo. LGI1 mimetic was delivered by daily intraperitoneal injection to C57/bl6 mice at high (100 ug/kg/day), medium (10 ug/kg/day) and low dose (1 ug/kg/day) for 30 days. No effect was seen on animal health or weight.
Figure 1:
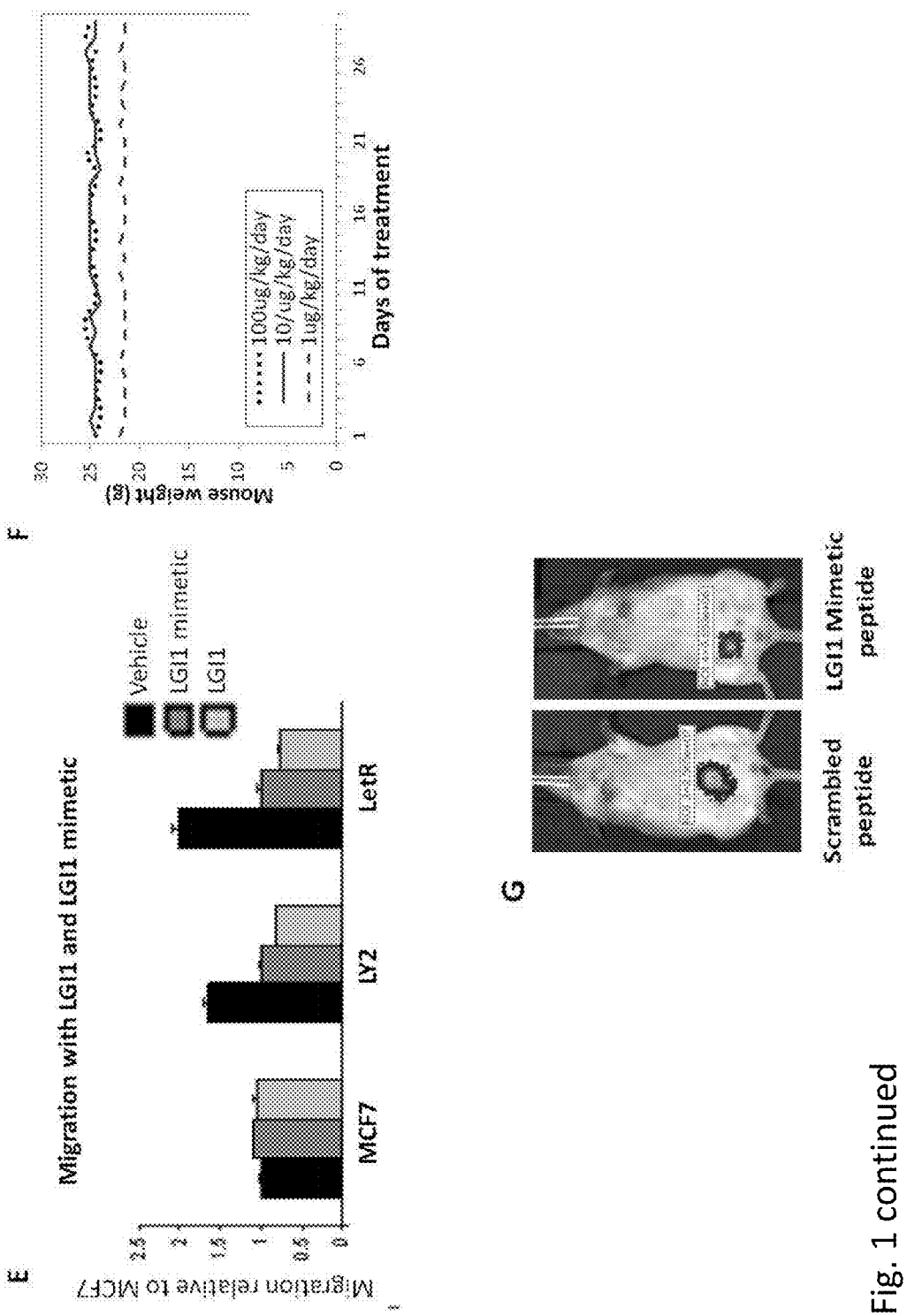

"ADAM22": This refers to any isoform of the transmembrane glycoprotein ADAM22 (A Disintegrin And Metalloproteinase 22) which has been identified as a SRC-1 transcriptional target specific to the resistant phenotype (FIG. 1A). The amino acid sequence of isoform 4 of the protein is provided in SEQ ID NO: 2:

Homo sapiens ADAM metallopeptidase domain 22 (ADAM22), transcript variant 4 Accession number: NM_004194

(SEQ ID NO: 2)
MQAAVAVSVPFLLLCVLGTCPPARCGQAGDASLMELEKRKENRFVERQSI

VPLRLIYRSGGEDESRHDALDTRVRGDLGGPQLTHVDQASFQVDAFGTSF

ILDVVLNHDLLSSEYIERHIEHGGKTVEVKGGEHCYYQGHIRGNPDSFVA

LSTCHGLHGMFYDGNHTYLIEPEENDTTQEDFHFHSVYKSRLFEFSIDDL

PSEFQQVNITPSKFILKPRPKRSKRQLRRYPRNVEEETKYIELMIVNDHL

MFKKHRLSVVHTNTYAKSVVNMADLIYKDQLKTRIVLVAMETWATDNKFA

ISENPLITLREFMKYRRDFIKEKSDAVHLFSGSQFESSRSGAAYIGGICS

LLKGGGVNEFGKTDLMAVTLAQSLAHNIGIISDKRKLASGECKCEDTWSG

CIMGDTGYYLPKKFTQCNIEEYHDFLNSGGGACLFNKPSKLLDPPECGNG

FIETGEECDCGTPAECVLEGAECCKKCTLTQDSQCSDGLCCKKCKFQPMG

TVCREAVNDCDIRETCSGNSSQCAPNIHKMDGYSCDGVQGICFGGRCKTR

DRQCKYIWGQKVTASDKYCYEKLNIEGTEKGNCGKDKDTWIQCNKRDVLC

GYLLCTNIGNIPRLGELDGEITSTLVVQQGRTLNCSGGHVKLEEDVDLGY

VEDGTPCGPQMMCLEHRCLPVASFNFSTCLSSKEGTICSGNGVCSNELKC

VCNRHWIGSDCNTYFPHNDDAKTGITLSGNGVAGTNIIIGIIAGTILVLA

LILGITAWGYKNYREQRQLPQGDYVKKPGDGDSFYSDIPPGVSTNSASSS

KKRSNGLSHSWSERIPDTKHISDICENGRPRSNSWQGNLGGNKKKIRGKR

FRPRSNSTE

The DNA sequence of the ADAM22-encoding genes (several isoform variants exist) include:

NM_021723: ADAM22 (uc003ujp.1) at chr7:87564071-87811339—ADAM metallopeptidase domain 22 isoform 4

NM_016351: ADAM22 (uc003ujo.2) at chr7:87563702-87826447—ADAM metallopeptidase domain 22 isoform 3

NM_021723: ADAM22 (uc003ujn.2at chr7:87563702-87826447—ADAM metallopeptidase domain 22 isoform 1

NM_021722: ADAM22 (uc003ujm.2) at chr7:87563702-87826447—ADAM metallopeptidase domain 22 isoform 2

NM_021721: ADAM22 (uc003ujl.1) at chr7:87563702-87811428—ADAM metallopeptidase domain 22 isoform 5

NM_004194: ADAM22 (uc003ujk.1) at chr7:87563702-87811428—ADAM metallopeptidase domain 22 isoform 4

NM_021721: ADAM22 (uc003ujj.1) at chr7:87563702-87762113—ADAM metallopeptidase domain 22 isoform 5

NM_021721: ADAM22 (uc003uji.1) at chr7:87563702-87757991—ADAM metallopeptidase domain 22 isoform 5

"Metastatic potential": This term should be understood to mean the potential of primary breast cancer to develop a metastatic phenotype leading to recurrence of the breast cancer.

"Expression of ADAM22": This term should be understood to mean positive detection of ADAM22 in breast cancer tumour tissue. Detection may be performed by means of full face tissue section or breast tumour sample tissue microarray (TMA) constructed and data recorded as described previously[1]. Tissue is immunostained using mouse anti ADAM22 (H00053616-B01). Positive detection is taken to be an Allred Score of greater than 3, as within the meaning of the assays of the invention[2]. Other methods of detecting expression of ADAM22 will be apparent to those skilled in the art.

"ADAM22 negative": This term means that ADAM22 expression cannot be positively detected in the breast cancer tumour sample using the immunostained tissue described and referenced above.

"ADAM22 positive": This term means that ADAM22 expression can be positively detected in the breast cancer tumour sample using the immunostained tissue described and referenced above.

"Treatment": This term means its generally accepted meaning which encompasses prohibiting, preventing, restraining, and slowing, stopping or reversing progression or severity of a metastatic breast cancer phenotype.

"Breast cancer patient" or "patient": This term means a patient who has a primary breast cancer tumour and awaits treatment for the cancer or has already undergone or is undergoing treatment for the primary tumour. The term should also be understood to include a patient who has had a primary breast cancer and is in remission, for example remission following treatment including one or more of tumour resection, first line chemotherapy, or both. Usually, the patient will be a breast cancer patient who has, or is undergoing, treatment for a primary tumour and who has been identified as having potential for developing a metastatic phenotype. In one embodiment, the patient has an ER-positive breast cancer.

"Administering": ADAM22 inhibitors, or pharmaceutical compositions of the invention, can be administered orally, parenterally, topically, rectally, nasally, buccally, via an implanted reservoir, or via inhalation spray. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. A sterile injectable composition, e.g., a sterile injectable aqueous or oleaginous suspension, can be formulated according to techniques known in the art using suitable dispersing or wetting agents (such as Tween 80) or suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation. A composition for oral administration can be any orally acceptable dosage form including, but not limited to, capsules, tablets, emulsions and aqueous suspensions, dispersions and solutions. In the case of tablets/capsules for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation.

"Therapeutically effective amount": This term refers to the amount or dose of the inhibitor or agent, upon single or multiple dose administration to the patient, which provides the desired effect in the patient under treatment. An effective amount can be readily determined by the attending diagnostician, as one skilled in the art, by the use of known techniques and by observing results obtained under analogous circumstances. In determining the effective amount or dose of inhibitor or agent administered, a number of factors are considered by the attending diagnostician, including, but not limited to: the species of mammal; its size, age, and general health; the degree of or involvement or the severity of the disease; the response of the individual patient; the particular inhibitor or agent administered; the mode of administration; the bioavailability characteristics of the preparation administered; the dose regimen selected; the use of concomitant medication; and other relevant circumstances. In particular, the term should be understood to mean a sufficient amount of ADAM22 inhibitor or agent to prevent or slow the development of a metastatic phenotype in a breast cancer patient.

"ADAM22 inhibitor": This term refers to a molecule capable of reducing cell migration and/or restoring differentiation in an endocrine resistant cell line selected from LY2 or LetR. The term should be understood to include an agent that attenuates the expression of ADAM22 protein (i.e. interferes with expression of the ADAM22 gene), including suppression of transcription or translation, and/or a molecule that directly inhibits ADAM22 activity, for example by binding to the ADAM22 protein (ADAM22 inhibitor ligand), especially the LGI1 binding site of ADAM22. Thus, in embodiment, the ADAM22 inhibitor is an ADAM22 ligand, typically capable of binding to the LGI1 binding site of ADAM22. The ADAM22 inhibitor ligand may be an ADAM22 antibody or peptide capable of binding to ADAM22 and inhibiting ADAM22 activity. Inhibitors which attenuate the expression of ADAM22 protein are known in the technical field and may comprise any of the group comprising siRNA (i.e. Ambion 4390824), miRNA, shRNA, antisense oligonucleotides, and ribozymes. Expression of ADAM22 may be suppressed by means of RNA interference (RNAi). RNA interference (RNAi) is an evolutionarily highly conserved process of post-transcriptional gene silencing (PTGS) by which double stranded RNA (known as siRNA molecules), when introduced into a cell, causes sequence-specific degradation of mRNA sequences. The RNAi machinery, once it finds a double-stranded RNA molecule, cuts it up, separates the two strands, and then proceeds to destroy RNA molecules that are complementary to one of those segments, or prevent their translation into proteins. Thus, suppression of ADAM22 expression may be achieved by treating an individual with siRNA molecules designed to target ADAM22 mRNA, preferably human ADAM22 and preferably a sequence in the human ADAM22 mRNA sense strand[1]. Five transcript variants of human ADAM22 mRNA are described, namely transcript variant 3, mRNA, NM_016351.4, transcript variant 2, mRNA, NM_021722.4, transcript variant 4, mRNA, NM_004194.3, transcript variant 1, mRNA, NM_021723.3, and transcript variant 5, mRNA, NM_021721.3.

Other types of gene knockdown tools will be well known to the person skilled in the field of molecular biology. For example, micro RNA's (miRNAs) are small (~22 nt) non-coding RNAs (ncRNAs) that regulate gene expression at the level of translation. Each miRNA apparently regulates multiple genes and hundreds of miRNA genes are predicted to be present in mammals. Recently miRNAs have been found to be critical for development, cell proliferation and cell development, apoptosis and fat metabolism, and cell differentiation. Alternatively, small hairpin RNA (shRNA) molecules are short RNA molecules having a small hairpin loop in their tertiary structure that may be employed to silence genes. The design of miRNA or shRNA molecules capable of silencing ADAM22 will be apparent to those skilled in the field of miRNA or shRNA molecule design. As an alternative, the level of ADAM22 expression can be modulated using antisense or ribozyme approaches to inhibit or prevent translation of ADAM22 mRNA transcripts or triple helix approaches to inhibit transcription of the ADAM22 gene. Antisense approaches involve the design of oligonucleotides (either DNA or RNA) that are complementary to ADAM mRNA. The antisense oligonucleotides will bind to the complementary mRNA transcripts and prevent translation.

Proteins that bind to ADAM22 and inhibit ADAM22 activity are also known in the field, and include the neuronal protein and known ADAM22 ligand LGI1 (SEQ ID NO: 1) and variants thereof described in the literature, for example LGI4[10].

LGI1 GENBANK® Number: AAQ89244

```
                                                  (SEQ ID NO: 1)
meserskrmg naciplkria yflcllsall ltegkkpakp kcpavctctk dnalcenars iprtvppdvi slsfvrsgft eisegsflft pslqlllfts nsfdvisdda figlphleyl fiennniksi srhtfrglks lihlslannn lqtlpkdifk gldsltnvdl rgnsfncdck lkwlvewlgh tnatvediyc egppeykkrk inslsskdfd ciitefaksq dlpyqslsid tfsylndeyv viaqpftgkc iflewdhvek tfrnydnitg tstvvckpiv ietqlyviva qlfggshiyk rdsfankfik iqdieilkir kpndieftki ennwyfvvad sskagfttiy kwngngfysh qslhawyrdt dveyleivrt pqtlrtphli
```

```
lssssqrpvi yqwnkatqlf tnqtdipnme dvyavkhfsv kgdvyicltr figdskvmkw ggssfqdiqr mpsrgsmvfq plqinnyqya ilgsdysftq vynwdaekak fvkfqelnvq aprsfthvsi nkrnflfass fkgntqiykh vivdlsa
```

LGI1 serves as a specific extracellular ligand for ADAM22[3]. The ADAM22 binding domain of LGI1 is known and consists of the sequence:

```
                                        (SEQ ID NO: 3)
    KGDVYICLTRFIGDSKVMKWGGSSFQDIQRMPSR.
```

This domain of LGI1 binds to

```
                                        (SEQ ID NO: 2)
                    ADAM22
``` at the LGI1 binding domain which is described in the literature

```
                                        (SEQ ID NO: 4)
    (CREAVNDCDIRETCSGNSSQCAPNIHKMDGYSCD).
```

Thus, ADAM22 inhibitors include LGI1 protein (and variants thereof capable of inhibiting migration of endocrine resistant breast cancer cells as determined in the motility assay described below) including LGI4[10], and LGI1 peptide mimics. As employed herein, the term "Inhibiting migration" should be understood as a significant reduction in migration, where significance is taken as p<0.05, as assessed using standard unpaired Student t-test[1].

"LGI1 peptide mimic": This term refers to a polymer composed of up to 100 amino acid monomers via peptide bond linkage, which is capable of mimicking the ADAM22 binding activity of LGI1 by binding to an LGI1 binding domain of ADAM22 and which is capable of inhibiting migration of endocrine resistant breast cancer cells as determined in the Motility Assay described below. The term includes poly amino acids comprising the ADAM22 binding domain of LGI1 (SEQUENCE ID NO: 3), functional fragments of the ADAM22 binding domain of LGI1 (SEQUENCE ID NO: 3), and polyamino acids comprising functional variants of SEQUENCE ID NO: 3. Methods of determining if a peptide is capable of mimicking the ADAM22 binding activity of LGI1 will be apparent to a person skilled in the art, and include conventional peptide binding assay.

The term "in-vitro model of breast cancer cell migration" should be understood to mean the Motility Assay described below. "Functional fragments of ADAM22 binding domain of LGI1": This term means a fragment of the ADAM22 binding domain of LGI1 (SEQ ID NO: 3) having at least 15, preferably 20, amino acids, which is capable of binding to the LGI1 binding domain of ADAM22 and capable of inhibiting migration of endocrine resistant breast cancer cells as determined in the Motility Assay described below. Examples of functional fragments include the following fragments of SEQ ID NO: 3:

```
                                        (SEQ ID NO: 5)
    KGDVYICLTRFIGDSKVMKWGG;

(SEQ ID NO: 6)
    KGDVYISLTRFIGDSKVMKWGG;

(SEQ ID NO: 7)
    DVYICLTRFIGDSKVMKWGGSS;

(SEQ ID NO: 8)
    YICLTRFIGDSKVMKWGGSSFQ;

(SEQ ID NO: 9)
    CLTRFIGDSKVMKWGGSSFQDI;

(SEQ ID NO: 10)
    TRFIGDSKVMKWGGSSFQDIQR;

(SEQ ID NO: 11)
    FIGDSKVMKWGGSSFQDIQRMP;
    and (SEQ ID NO: 12)
    GDSKVMKWGGSSFQDIQRMPSR.
```

"Functional variants": This term means a variant of SEQUENCE ID NO: 3 (or a variant of a functional fragment) having at least 90% sequence homology with the SEQ ID NO: 3 or the fragment and which is capable of binding to the LGI1 binding domain of ADAM22 and capable of inhibiting migration of endocrine resistant breast cancer cells as determined in the motility assay described below. It shall be taken to mean peptides having amino acid sequences which are substantially identical to the fragment, and include peptides that are altered in respect of one or more amino acid residues compared to the fragment. An example is SEQ ID NO: 6, which is a function variant of the fragment of SEQ ID NO: 5. Preferably such alterations involve the insertion, addition, deletion and/or substitution of 5 or fewer amino acids, more preferably of 4 or fewer, even more preferably of 3 or fewer, most preferably of 1 or 2 amino acids only. Insertion, addition and substitution with natural and modified amino acids are envisaged. The variant may have conservative amino acid changes, wherein the amino acid being introduced is similar structurally, chemically, or functionally to that being substituted. The variant will have at least 90% sequence homology, and ideally at least 95%, 96%, 97%, 98% or 99% sequence homology with the fragment. In this context, sequence homology comprises both sequence identity and similarity, i.e. a polypeptide sequence that shares 90% sequence homology with a specific LGI1 fragment is one in which any 90% of aligned residues are either identical to, or conservative substitutions of, the corresponding residues in the LGI1 fragment.

Peptides (including variants and fragments thereof) of and for use in the invention may be generated wholly or partly by chemical synthesis or by expression from nucleic acid. The peptides of and for use in the present invention can be readily prepared according to well-established, standard liquid or, preferably, solid-phase peptide synthesis methods known in the art (see, for example Young[4]). When necessary, any of the LGI1 peptide mimics described herein can be chemically modified, for example to increase their stability. A chemically modified peptide (a peptide analog) includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2,4,6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

"Pharmaceutically acceptable carrier": Any of the breast cancer treatments described herein can be mixed with a pharmaceutically acceptable carrier to form a pharmaceutical composition. "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

Embodiments of the invention also provide for systems (and computer readable media for causing computer systems) to perform a method for diagnosing metastatic potential of a breast cancer in an individual or to perform a method for identifying a breast cancer patient suitable for treatment or prevention of metastatic breast cancer with an ADAM22 inhibitor.

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable storage media may define instructions, for example, as part of one or more programs, that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable storage media on which such instructions are embodied may reside on one or more of the components of either of a system, or a computer readable storage medium described herein, may be distributed across one or more of such components.

The computer-readable storage media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include at minimum a determination system, a storage device, optionally a comparison module, and a display module. The functional modules can be executed on one, or multiple, computers, or by using one, or multiple, computer networks. The determination system has computer executable instructions to provide e.g., ADA22 expression levels in computer readable form.

The determination system, can comprise any system for assaying a breast cancer tumor sample for expression of ADAM22. Standard procedures such as immunohistochemistry, may be employed.

The information determined in the determination system can be read by the storage device. As used herein the "storage device" is intended to include any suitable computing or processing apparatus or other device configured or adapted for storing data or information. Examples of an electronic apparatus suitable for use with the present invention include a stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device is adapted or configured for having recorded thereon nucleic acid sequence information. Such information may be provided in digital form that can be transmitted and read electronically, e.g., via the Internet, on diskette, via USB (universal serial bus) or via any other suitable mode of communication.

As used herein, "stored" refers to a process for encoding information on the storage device. Those skilled in the art can readily adopt any of the presently known methods for recording information on known media to generate manufactures comprising information relating to ADAM22 expression in a sample.

In one embodiment the reference data stored in the storage device to be read by the comparison module is compared.

The "comparison module" can use a variety of available software programs and formats for the comparison operative to compare ADAM22 expression information data determined in the determination system to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, staining, and may be optimized for particular data comparisons that are conducted. The comparison module provides computer readable information related to the ADAM22 expression levels of the sample.

The comparison module, or any other module of the invention, may include an operating system (e.g., UNIX®) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GENBANK® or SWISS-PROT® World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content based in part on the comparison result that may be stored and output as requested by a user using a display module.

In one embodiment of the invention, the content based on the comparison result or the determination system is displayed on a computer monitor. In one embodiment of the invention, the content based on the comparison result or determination system is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The methods described herein therefore provide for systems (and computer readable media for causing computer systems) to perform methods as described in the Statements of Invention above, for example methods for diagnosing metastatic potential of a breast cancer in an individual or methods for identifying a breast cancer patient suitable for treatment or prevention of metastatic breast cancer with an ADAM22 inhibitor.

Systems and computer readable media described herein are merely illustrative embodiments of the invention for performing methods of diagnosis in an individual, and are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

EXPERIMENTAL

The invention identifies the disintegrin ADAM22, as a prognostic biomarker of breast cancer metastatic disease.

The invention also relates to the use of LGI1 (the natural ligand of ADAM22) or a peptide mimetic thereof, which is functional and can inhibit migration in breast cancer cells. The invention also relates to the use of LGI1 or a peptide mimetic of LGI1 as a potential therapy for the treatment or prevention of metastatic breast cancer optionally in combination with a companion diagnostic for ADAM22, providing directed personalised treatment for patients with recurrent disease.

Endocrine therapies, including tamoxifen and aromatase inhibitors, are first-line treatments for estrogen receptor-positive breast cancer. Although most patients initially respond, approximately 30% develop metastatic disease. There is no effective treatment for endocrine-related tumour metastasis, hence a social and economic need exists to identify patients likely to develop resistance and to discover new drug targets. Studies by our group and others have established that aberrant expression of the SRC-1, is central to the resistant phenotype and development of metastasis. The applicant used SRC-1 ChIP-Seq, expression arrays and bioinformatic analysis to generate a list of SRC-1 target genes representing novel potential druggable targets relevant to treating metastatic disease.

The transmembrane glycoprotein ADAM22 (A Disintegrin And Metalloproteinase 22) was identified as a SRC-1 transcriptional target specific to the resistant phenotype[1]. ADAM22 was found to be expressed in both endocrine resistant (LY2 and LetR) and insensitive (MDA-MB-231) cells. SRC-1 can regulate ADAM22 in endocrine sensitive and resistant cells. Furthermore, it has been established that ADAM22 is a significant independent prognostic indicator of poor disease-free survival in breast cancer patients[1]. The Applicant has demonstrated that knockdown of ADAM22 with siRNA reduced cell migration and restored differentiation in endocrine resistant cell[1] (FIGS. 1A and B). Additionally, in xenograft studies, expression of ADAM22 was absent from both the 4-OHT treated and untreated sensitive tumours and from the untreated resistant tumours[1]. Data from these studies firmly implicate ADAM22 in the development of metastatic breast disease and suggest ADAM22 as a viable drug target for the treatment of endocrine resistant breast cancer.

As ADAM22 expression has previously only been described in the central nervous system, a therapeutic directed against systemic ADAM22 has the potential to be highly specific for the breast and have low toxicity. The neuronal protein, LGI1 serves as a specific extracellular ligand for ADAM22[4]. It functions as a tumour suppressor of glioblastoma and neuroblastoma and recently has been shown to impair proliferation in HeLa cells[5-8]. The LGI1/ADAM22 ligand/receptor complex has been suggested as a therapeutic target for synaptic disorders. The Applicant has shown that treatment with recombinant LGI1 reduced cellular migration and restored differentiation in endocrine resistant cells in a similar manner to that observed with knockdown of ADAM22 (FIGS. 1C and D). A 22 amino acid peptide mimetic of LGI1 with a simple hairpin structure against the active binding domain of ADAM22 has been developed. The Applicant demonstrates that this peptide mimetic of LGI1 can reduce cell migration in metastatic and endocrine resistant breast cancer cells, in a similar manner to full length LGI1 and siADAM22 (FIG. 1E). In vivo studies have been undertaken to assess the efficacy of the LGI1 mimetic in reducing breast cancer burden in endocrine resistant breast cancer. In preliminary studies the LGI1 peptide was shown to be well tolerated with no toxicity observed (FIG. 1F). In a xenograft model of endocrine resistance, LGI1 significantly reduced tumour burden (FIG. 1G). These data demonstrate the potential of a mimetic of LGI1 as a new directed therapy to treat endocrine related tumour metastasis with its receptor ADAM22 acting as a companion diagnostic. This has significant advantage over previous methods described of detecting metastatic disease[9].

Motility Assay

A. Cell Preparation

For cell culture use Minimum Essential Medium-Eagle (EMEM; BioWhittaker, Product No. 12-611Q) containing the following supplements (=EMEM Complete Medium): 10% fetal calf serum (BioWhittaker, Product No. 14-503F), 1X penicillin/streptomycin solution (BioWhittaker, Product No. 17-602E), 1% L-glutamine (BioWhittaker, Product No. 17-605E), 1% non-essential amino acids (BioWhittaker, Product No. 13-114E) and 1% sodium pyruvate (BioWhittaker, Product No. 13-115E).

Split cells when they reach 60-80% confluency (every 2-3 days), diluting 1:5 to 1:10.

For cell motility, harvest cells with trypsin-versene mixture (BioWhittaker, Product No. 17-161F) and dilute into EMEM Complete Medium (warmed to 37° C.). For cells cultured in a T-75 flask, wash cells with 3 ml of trypsin. Add another 3 ml of trypsin and aspirate 2 ml. Allow cells to detach by incubating flask at 37° C. for 5 minutes and then add 9 ml of EMEM Complete Medium and centrifuge cells at 400×g for 5 minutes at room temperature.

Wash 3× with Serum-Free Culture Medium (warmed to 37° C.) (see Procedure section).

Adjust cell density to $10^4$ cells/ml in EMEM serum-free medium and add 50 µl of the cell suspension to each well of a 96-well microplate (=500 cells/well). Cell motility is stimulated with 50 µl of 10% fetal bovine serum (FBS) diluted in EMEM serum-free medium. See Procedure section.

Incubate for desired time at 37° C. in 5% CO2 (22 hours for MCF-7 derived cells)

B. Procedure

Note: Use 100 µl per well unless indicated otherwise. The protocol requires ~2.5 hours post-compound incubation to perform.

1. Suspend the Blue Fluorescent Microspheres (1 tube per 96-well plate) by vortexing for 30 seconds. Centrifuge the microspheres for 1 minute at 20,000×g. The highest speed on a standard microcentrifuge is generally sufficient.
2. Aspirate supernatant, add 0.5 ml 1× Wash Buffer and completely suspend beads by vortexing on maximum speed for at least 30 seconds.
3. Centrifuge for 1 minute at 20,000×g.
4. Aspirate supernatant, add 0.5 ml 1× Wash Buffer and completely resuspend beads by vortexing on maximum speed forat least 30 seconds.
5. Transfer the Blue Fluorescent Microsphere solution to a tube containing 7.5 ml 1× Wash Buffer, vortex on maximum speed for 60 seconds and immediately add 75 µl to each well of a 96-well plate coated with the desired substrate (For MCF-7 derived cells, type I collagen).
6. Incubate plate for 1 hour at 37° C. in the dark.
7. Wash plate five times with 200 µl of 1× Wash Buffer, removing each wash by aspiration. Leave buffer from last wash in wells. Plates may be stored in this format at 4° C. for up to 1 week.
8. Harvest L929 cells as described in Cell Preparation Section.

9. Centrifuge cells at 400×g for 5 minutes at room temperature. Resuspend cells in 10 ml Serum-Free Culture Medium, pre-warmed to 37° C. Washing the cells in the absence of serum is essential to prevent stimulation of cell motility.
10. Repeat step 9 two more times and dilute cells to 104 cells/ml in Serum-Free Culture Medium. Use 6 ml of the cell suspension per plate.
11. Warm the Blue Fluorescent Microsphere plates to 37° C. Aspirate Wash Buffer from plates (as prepared in steps 1-7), and gently add 50 μl (5×102 cells) of the cell suspension to each well. Low cell seeding densities are important for minimizing overlapping of tracks. If test compound is known to prevent cell attachment, for best results pre-incubate cells at 37° C. to let cells attach before motility stimulation/inhibition.
12. Add 50 μl of Serum-Free Culture Medium containing supplements for negative controls or 50 μl of 10% FBS in EMEM Serum-Free Medium for positive controls (for a final concentration of 5% serum) to each well. Serum is a stimulator of cell motility. When screening for cell motility antagonists, add test compounds before or during serum addition.
13. Incubate for desired time (e.g., 22 hours) at 37° C. in 5% $CO_2$.
14. Add 200 μl of 5.5% warmed Fixation Solution to each well and incubate in fume hood at room temperature for 60 minutes. Do not remove medium before adding the Fixation Solution. Using warm Fixation Solution is critical to maintaining cell integrity.
15. Aspirate Fixation Solution and wash plate three times with 100 μl of 1× Wash Buffer.
16. Aspirate Wash Buffer and add 100 μl of 1× Permeabilization Buffer and incubate for 15 minutes at room temperature.
17. Aspirate Permeabilization Buffer, add 100 μl Staining Solution and incubate for 30 minutes at room temperature.
18. Aspirate Staining Solution and wash wells three times with 100 μl 1× Wash Buffer. Aspirate the last wash and fill wells with 200 μl 1× Wash Buffer.
19. Seal plate and evaluate on the ArrayScan HCS Reader. Store sealed plates in the dark at 4° C.

Immunohistochemistry Methods

Immunohistochemistry is the localization of antigens in tissue sections by the use of labelled antibodies as specific reagents through antigen-antibody interactions that are visualized by a marker such as an enzyme or a fluorescent label. An unlabelled primary antibody is incubated on the tissue section, binding the antigen of interest. A biotinylated secondary antibody directed against the primary antibody is then applied. A strepavidinbiotin complex (ABC) which possesses biotin binding sites is then added, cross reacts with the biotin molecules on the secondary antibody, amplifying the signal intensity. A slide comprising the tissue section is evaluated by light microscopy using the Allred System described in Harvey et al[2]. First, a proportion score was assigned, which represented the estimated proportion of tumour cells staining positive for ADAM 22 [3 (0, none; 1, <1/100; 2, 1/100 to 1/10; 3, 1/10 to 1/3; 4, 1/3 to 2/3; and 5, >2/3). Next, an intensity score was assigned which represented the average intensity of positive tumour cells (0, none; 1, weak, 2, intermediate; and 3, strong). The proportion and intensity scores were then added to obtain a total score, which ranged from 0 to 8. A score of 3 or greater represents a positive detection within the meaning of the assays of the invention.

The invention pertains to a marker of breast tumour metastasis that can be detected in patient tissue that can also be used as a drug target. A routine immunohistochemical based test for ADAM22 will significantly predict the propensity of the tumour to metastasise and is a potential source of revenue. The test is typically performed on paraffin embedded patient tissue taken at the time of initial surgery for the removal of the tumour. A positive test result indicates poor disease free survival.

REFERENCES

1. McCartan D, Bolger J, Fagan A. et al. Global characterization of the SRC-1 transcriptome identifies ADAM22 as an ER-independent mediator of endocrine resistant breast cancer. Cancer Res. 2012; 72:220-9
2. Dillon M F, Stafford A T, Kelly G, Redmond A M, McIlroy M, Crotty T B, et al. Cyclooxygenase-2 predicts adverse effects of tamoxifen: a possible mechanism of role for nuclear HER2 in breast cancer patients. Endocr Relat Cancer. 2008, 15:745-53
3. Harvey J M, Clark G M, Osborne C K, Allred D C. Estrogen receptor status by immunohistochemistry is superior to the ligand-binding assay for predicting response to adjuvant endocrine therapy in breast cancer. J Clin Oncol. 1999, 17:1474-81. 3. Fukata Y, Adesnik H, Iwanaga T, Bredt D S, Nicoll R A, Fukata M. Epilepsy-related ligand receptor complex LGI1 and ADAM22 regulate synaptic transmission. Science 2006; 313, 1792-95.
4. J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984)
5. Gabellini N, Masola V, Quartesan S et al. Increased expression of LGI1 gene triggers growth inhibition and apoptosis of neuroblastoma cells. J Cell Physiol 2006; 207, 711-721.
6. Gabellini N, Masola V. Expression of LGI1 impairs proliferation and survival of Hela cells. Int J Cell Biol 2009, 417197. 7. Kunapuli P, Kasyapa C S, Hawthorn L, Cowell J K. LGI1, a putative tumour metastasis suppressor gene, controls in vitro invasiveness and expression of matrix metalloproteinase in glioma cells through the ERK1/2 pathway. J Biol Chem 2004; 279, 23151-23157.
7. Kunapuli P, Kasyapa C S, Hawthorn L, Cowell J K. LGI1, a putative tumor metastasis suppressor gene, controls in vitro invasiveness and expression of matrix metalloproteinases in glioma cells through the ERK1/2 pathway. J Biol Chem. 2004 May 28; 279(22):23151-7. Epub 2004 Mar. 26.
8. Fukata Y, Adesnik H, Iwanaga T, Bredt D S, Nicoll R A, Fukata M. Epilepsy-related ligand/receptor complex LGI1 and ADAM22 regulate synaptic transmission. Science. 2006 Sep. 22; 313(5794):1792-5
9. US 2005/221376 A1 (Young Paul E [US] ET AL) 6 Oct. 2005 (2005-10-06). 10. Sagane K, Int J Biol Sci 2008; 4(6): 387-396

The invention claimed is:

1. A method for treating metastatic breast cancer in a patient, comprising administering to the patient a therapeutically effective amount of an ADAM22 antibody, wherein the antibody binds to ADAM22, inhibits ADAM22 activity, and inhibits migration of endocrine resistant breast cancer cells, wherein breast tumor tissue from the patient is ADAM22-positive.

2. The method of claim 1, wherein the patient has ER positive breast cancer.

3. The method of claim 1, wherein the ADAM22 antibody is an antibody that reduces cell migration in an endocrine resistant cell line selected from LY2 or LetR.

4. The method of claim 1, wherein the metastatic breast cancer in the patient is endocrine resistant metastatic breast cancer.

* * * * *

SEQUENCE LISTING

<160> NUMBER OF SEQ ID NOS: 12

<210> SEQ ID NO 1
<211> LENGTH: 557
<212> TYPE: PRT
<213> ORGANISM: Homo sapiens
<220> FEATURE:
<221> NAME/KEY: MISC_FEATURE
<222> LOCATION: (1)..(557)
<223> OTHER INFORMATION: LGI1 protein

<400> SEQUENCE: 1

Met Glu Ser Glu Arg Ser Lys Arg Met Gly Asn Ala Cys Ile Pro Leu
1               5                   10                  15

Lys Arg Ile Ala Tyr Phe Leu Cys Leu Leu Ser Ala Leu Leu Leu Thr
            20                  25                  30

Glu Gly Lys Lys Pro Ala Lys Pro Lys Cys Pro Ala Val Cys Thr Cys
        35                  40                  45

Thr Lys Asp Asn Ala Leu Cys Glu Asn Ala Arg Ser Ile Pro Arg Thr
    50                  55                  60

Val Pro Pro Asp Val Ile Ser Leu Ser Phe Val Arg Ser Gly Phe Thr
65                  70                  75                  80

Glu Ile Ser Glu Gly Ser Phe Leu Phe Thr Pro Ser Leu Gln Leu Leu
                85                  90                  95

Leu Phe Thr Ser Asn Ser Phe Asp Val Ile Ser Asp Asp Ala Phe Ile
            100                 105                 110

Gly Leu Pro His Leu Glu Tyr Leu Phe Ile Glu Asn Asn Asn Ile Lys
        115                 120                 125

Ser Ile Ser Arg His Thr Phe Arg Gly Leu Lys Ser Leu Ile His Leu
    130                 135                 140

Ser Leu Ala Asn Asn Asn Leu Gln Thr Leu Pro Lys Asp Ile Phe Lys
145                 150                 155                 160

Gly Leu Asp Ser Leu Thr Asn Val Asp Leu Arg Gly Asn Ser Phe Asn
                165                 170                 175

Cys Asp Cys Lys Leu Lys Trp Leu Val Glu Trp Leu Gly His Thr Asn
            180                 185                 190

Ala Thr Val Glu Asp Ile Tyr Cys Glu Gly Pro Pro Glu Tyr Lys Lys
        195                 200                 205

Arg Lys Ile Asn Ser Leu Ser Ser Lys Asp Phe Asp Cys Ile Ile Thr
    210                 215                 220

Glu Phe Ala Lys Ser Gln Asp Leu Pro Tyr Gln Ser Leu Ser Ile Asp
225                 230                 235                 240

Thr Phe Ser Tyr Leu Asn Asp Glu Tyr Val Val Ile Ala Gln Pro Phe
                245                 250                 255

Thr Gly Lys Cys Ile Phe Leu Glu Trp Asp His Val Glu Lys Thr Phe
            260                 265                 270

Arg Asn Tyr Asp Asn Ile Thr Gly Thr Ser Thr Val Cys Lys Pro
        275                 280                 285

Ile Val Ile Glu Thr Gln Leu Tyr Val Ile Val Ala Gln Leu Phe Gly
    290                 295                 300

Gly Ser His Ile Tyr Lys Arg Asp Ser Phe Ala Asn Lys Phe Ile Lys
305                 310                 315                 320

Ile Gln Asp Ile Glu Ile Leu Lys Ile Arg Lys Pro Asn Asp Ile Glu
                325                 330                 335

Thr Phe Lys Ile Glu Asn Asn Trp Tyr Phe Val Val Ala Asp Ser Ser
            340                 345                 350

```
Lys Ala Gly Phe Thr Thr Ile Tyr Lys Trp Asn Gly Asn Gly Phe Tyr
            355                 360                 365

Ser His Gln Ser Leu His Ala Trp Tyr Arg Asp Thr Asp Val Glu Tyr
        370                 375                 380

Leu Glu Ile Val Arg Thr Pro Gln Thr Leu Arg Thr Pro His Leu Ile
385                 390                 395                 400

Leu Ser Ser Ser Gln Arg Pro Val Ile Tyr Gln Trp Asn Lys Ala
                405                 410                 415

Thr Gln Leu Phe Thr Asn Gln Thr Asp Ile Pro Asn Met Glu Asp Val
            420                 425                 430

Tyr Ala Val Lys His Phe Ser Val Lys Gly Asp Val Tyr Ile Cys Leu
            435                 440                 445

Thr Arg Phe Ile Gly Asp Ser Lys Val Met Lys Trp Gly Ser Ser
            450                 455                 460

Phe Gln Asp Ile Gln Arg Met Pro Ser Arg Gly Ser Met Val Phe Gln
465                 470                 475                 480

Pro Leu Gln Ile Asn Asn Tyr Gln Tyr Ala Ile Leu Gly Ser Asp Tyr
                485                 490                 495

Ser Phe Thr Gln Val Tyr Asn Trp Asp Ala Glu Lys Ala Lys Phe Val
            500                 505                 510

Lys Phe Gln Glu Leu Asn Val Gln Ala Pro Arg Ser Phe Thr His Val
            515                 520                 525

Ser Ile Asn Lys Arg Asn Phe Leu Phe Ala Ser Ser Phe Lys Gly Asn
            530                 535                 540

Thr Gln Ile Tyr Lys His Val Ile Val Asp Leu Ser Ala
545                 550                 555

<210> SEQ ID NO 2
<211> LENGTH: 859
<212> TYPE: PRT
<213> ORGANISM: Homo sapiens
<220> FEATURE:
<221> NAME/KEY: MISC_FEATURE
<222> LOCATION: (1)..(342)
<223> OTHER INFORMATION: ADAM22 protein

<400> SEQUENCE: 2

Met Gln Ala Ala Val Ala Val Ser Val Pro Phe Leu Leu Cys Val
1               5                   10                  15

Leu Gly Thr Cys Pro Pro Ala Arg Cys Gly Gln Ala Gly Asp Ala Ser
            20                  25                  30

Leu Met Glu Leu Glu Lys Arg Lys Glu Asn Arg Phe Val Glu Arg Gln
        35                  40                  45

Ser Ile Val Pro Leu Arg Leu Ile Tyr Arg Ser Gly Gly Glu Asp Glu
    50                  55                  60

Ser Arg His Asp Ala Leu Asp Thr Arg Val Arg Gly Asp Leu Gly Gly
65                  70                  75                  80

Pro Gln Leu Thr His Val Asp Gln Ala Ser Phe Gln Val Asp Ala Phe
                85                  90                  95

Gly Thr Ser Phe Ile Leu Asp Val Val Leu Asn His Asp Leu Leu Ser
            100                 105                 110

Ser Glu Tyr Ile Glu Arg His Ile Glu His Gly Gly Lys Thr Val Glu
        115                 120                 125

Val Lys Gly Gly Glu His Cys Tyr Tyr Gln Gly His Ile Arg Gly Asn
    130                 135                 140
```

-continued

```
Pro Asp Ser Phe Val Ala Leu Ser Thr Cys His Gly Leu His Gly Met
145                 150                 155                 160
Phe Tyr Asp Gly Asn His Thr Tyr Leu Ile Glu Pro Glu Glu Asn Asp
                165                 170                 175
Thr Thr Gln Glu Asp Phe His Phe His Ser Val Tyr Lys Ser Arg Leu
            180                 185                 190
Phe Glu Phe Ser Leu Asp Asp Leu Pro Ser Glu Phe Gln Gln Val Asn
        195                 200                 205
Ile Thr Pro Ser Lys Phe Ile Leu Lys Pro Arg Pro Lys Arg Ser Lys
    210                 215                 220
Arg Gln Leu Arg Arg Tyr Pro Arg Asn Val Glu Glu Thr Lys Tyr
225                 230                 235                 240
Ile Glu Leu Met Ile Val Asn Asp His Leu Met Phe Lys Lys His Arg
                245                 250                 255
Leu Ser Val Val His Thr Asn Thr Tyr Ala Lys Ser Val Val Asn Met
            260                 265                 270
Ala Asp Leu Ile Tyr Lys Asp Gln Leu Lys Thr Arg Ile Val Leu Val
        275                 280                 285
Ala Met Glu Thr Trp Ala Thr Asp Asn Lys Phe Ala Ile Ser Glu Asn
    290                 295                 300
Pro Leu Ile Thr Leu Arg Glu Phe Met Lys Tyr Arg Arg Asp Phe Ile
305                 310                 315                 320
Lys Glu Lys Ser Asp Ala Val His Leu Phe Ser Gly Ser Gln Phe Glu
                325                 330                 335
Ser Ser Arg Ser Gly Ala Ala Tyr Ile Gly Gly Ile Cys Ser Leu Leu
            340                 345                 350
Lys Gly Gly Gly Val Asn Glu Phe Gly Lys Thr Asp Leu Met Ala Val
        355                 360                 365
Thr Leu Ala Gln Ser Leu Ala His Asn Ile Gly Ile Ile Ser Asp Lys
    370                 375                 380
Arg Lys Leu Ala Ser Gly Glu Cys Lys Cys Glu Asp Thr Trp Ser Gly
385                 390                 395                 400
Cys Ile Met Gly Asp Thr Gly Tyr Tyr Leu Pro Lys Lys Phe Thr Gln
                405                 410                 415
Cys Asn Ile Glu Glu Tyr His Asp Phe Leu Asn Ser Gly Gly Gly Ala
            420                 425                 430
Cys Leu Phe Asn Lys Pro Ser Lys Leu Leu Asp Pro Pro Glu Cys Gly
        435                 440                 445
Asn Gly Phe Ile Glu Thr Gly Glu Glu Cys Asp Cys Gly Thr Pro Ala
    450                 455                 460
Glu Cys Val Leu Glu Gly Ala Glu Cys Cys Lys Lys Cys Thr Leu Thr
465                 470                 475                 480
Gln Asp Ser Gln Cys Ser Asp Gly Leu Cys Cys Lys Lys Cys Lys Phe
                485                 490                 495
Gln Pro Met Gly Thr Val Cys Arg Glu Ala Val Asn Asp Cys Asp Ile
            500                 505                 510
Arg Glu Thr Cys Ser Gly Asn Ser Ser Gln Cys Ala Pro Asn Ile His
        515                 520                 525
Lys Met Asp Gly Tyr Ser Cys Asp Gly Val Gln Gly Ile Cys Phe Gly
    530                 535                 540
Gly Arg Cys Lys Thr Arg Asp Arg Gln Cys Lys Tyr Ile Trp Gly Gln
545                 550                 555                 560
Lys Val Thr Ala Ser Asp Lys Tyr Cys Tyr Glu Lys Leu Asn Ile Glu
```

```
                    565                 570                 575

Gly Thr Glu Lys Gly Asn Cys Gly Lys Asp Lys Asp Thr Trp Ile Gln
            580                 585                 590

Cys Asn Lys Arg Asp Val Leu Cys Gly Tyr Leu Leu Cys Thr Asn Ile
        595                 600                 605

Gly Asn Ile Pro Arg Leu Gly Glu Leu Asp Gly Glu Ile Thr Ser Thr
    610                 615                 620

Leu Val Val Gln Gln Gly Arg Thr Leu Asn Cys Ser Gly Gly His Val
625                 630                 635                 640

Lys Leu Glu Glu Asp Val Asp Leu Gly Tyr Val Glu Asp Gly Thr Pro
                645                 650                 655

Cys Gly Pro Gln Met Met Cys Leu Glu His Arg Cys Leu Pro Val Ala
            660                 665                 670

Ser Phe Asn Phe Ser Thr Cys Leu Ser Ser Lys Glu Gly Thr Ile Cys
        675                 680                 685

Ser Gly Asn Gly Val Cys Ser Asn Glu Leu Lys Cys Val Cys Asn Arg
    690                 695                 700

His Trp Ile Gly Ser Asp Cys Asn Thr Tyr Phe Pro His Asn Asp Asp
705                 710                 715                 720

Ala Lys Thr Gly Ile Thr Leu Ser Gly Asn Gly Val Ala Gly Thr Asn
                725                 730                 735

Ile Ile Ile Gly Ile Ile Ala Gly Thr Ile Leu Val Leu Ala Leu Ile
            740                 745                 750

Leu Gly Ile Thr Ala Trp Gly Tyr Lys Asn Tyr Arg Glu Gln Arg Gln
        755                 760                 765

Leu Pro Gln Gly Asp Tyr Val Lys Lys Pro Gly Asp Gly Asp Ser Phe
    770                 775                 780

Tyr Ser Asp Ile Pro Pro Gly Val Ser Thr Asn Ser Ala Ser Ser Ser
785                 790                 795                 800

Lys Lys Arg Ser Asn Gly Leu Ser His Ser Trp Ser Glu Arg Ile Pro
                805                 810                 815

Asp Thr Lys His Ile Ser Asp Ile Cys Glu Asn Gly Arg Pro Arg Ser
            820                 825                 830

Asn Ser Trp Gln Gly Asn Leu Gly Gly Asn Lys Lys Ile Arg Gly
        835                 840                 845

Lys Arg Phe Arg Pro Arg Ser Asn Ser Thr Glu
    850                 855

<210> SEQ ID NO 3
<211> LENGTH: 34
<212> TYPE: PRT
<213> ORGANISM: Homo sapiens
<220> FEATURE:
<221> NAME/KEY: MISC_FEATURE
<222> LOCATION: (1)..(34)
<223> OTHER INFORMATION: ADAM22 binding domain of LGI1

<400> SEQUENCE: 3

Lys Gly Asp Val Tyr Ile Cys Leu Thr Arg Phe Ile Gly Asp Ser Lys
1               5                   10                  15

Val Met Lys Trp Gly Gly Ser Phe Gln Asp Ile Gln Arg Met Pro
            20                  25                  30

Ser Arg

<210> SEQ ID NO 4
<211> LENGTH: 34
```

```
<212> TYPE: PRT
<213> ORGANISM: Homo sapiens
<220> FEATURE:
<221> NAME/KEY: MISC_FEATURE
<222> LOCATION: (1)..(34)
<223> OTHER INFORMATION: LGI1 binding domain of ADAM22

<400> SEQUENCE: 4

Cys Arg Glu Ala Val Asn Asp Cys Asp Ile Arg Glu Thr Cys Ser Gly
1               5                   10                  15

Asn Ser Ser Gln Cys Ala Pro Asn Ile His Lys Met Asp Gly Tyr Ser
            20                  25                  30

Cys Asp

<210> SEQ ID NO 5
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: Fragment of ADAM22 binding domain of LGI1

<400> SEQUENCE: 5

Lys Gly Asp Val Tyr Ile Cys Leu Thr Arg Phe Ile Gly Asp Ser Lys
1               5                   10                  15

Val Met Lys Trp Gly Gly
            20

<210> SEQ ID NO 6
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: Fragment of ADAM22 binding domain of LGI1

<400> SEQUENCE: 6

Lys Gly Asp Val Tyr Ile Ser Leu Thr Arg Phe Ile Gly Asp Ser Lys
1               5                   10                  15

Val Met Lys Trp Gly Gly
            20

<210> SEQ ID NO 7
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: Fragment of ADAM22 binding domain of LGI1

<400> SEQUENCE: 7

Asp Val Tyr Ile Cys Leu Thr Arg Phe Ile Gly Asp Ser Lys Val Met
1               5                   10                  15

Lys Trp Gly Gly Ser Ser
            20

<210> SEQ ID NO 8
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
```

<223> OTHER INFORMATION: Fragment of ADAM22 binding domain of LGI1

<400> SEQUENCE: 8

Tyr Ile Cys Leu Thr Arg Phe Ile Gly Asp Ser Lys Val Met Lys Trp
1               5                   10                  15

Gly Gly Ser Ser Phe Gln
            20

<210> SEQ ID NO 9
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: Fragment of ADAM22 binding domain of LGI1

<400> SEQUENCE: 9

Cys Leu Thr Arg Phe Ile Gly Asp Ser Lys Val Met Lys Trp Gly Gly
1               5                   10                  15

Ser Ser Phe Gln Asp Ile
            20

<210> SEQ ID NO 10
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: Fragment of ADAM22 binding domain of LGI1

<400> SEQUENCE: 10

Thr Arg Phe Ile Gly Asp Ser Lys Val Met Lys Trp Gly Gly Ser Ser
1               5                   10                  15

Phe Gln Asp Ile Gln Arg
            20

<210> SEQ ID NO 11
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: Fragment of ADAM22 binding domain of LGI1

<400> SEQUENCE: 11

Phe Ile Gly Asp Ser Lys Val Met Lys Trp Gly Gly Ser Ser Phe Gln
1               5                   10                  15

Asp Ile Gln Arg Met Pro
            20

<210> SEQ ID NO 12
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: Fragment of ADAM22 binding domain of LGI1

```
<400> SEQUENCE: 12

Gly Asp Ser Lys Val Met Lys Trp Gly Gly Ser Ser Phe Gln Asp Ile
1               5                   10                  15

Gln Arg Met Pro Ser Arg
            20
```